United States Patent
Gellert

(10) Patent No.: US 8,240,334 B2
(45) Date of Patent: Aug. 14, 2012

(54) ARRANGEMENT FOR METERING A GASEOUS SAMPLE IN A CARRIER GAS STREAM

(75) Inventor: Udo Gellert, Bellheim (DE)

(73) Assignee: Siemens Aktiengesellschaft, München (DE)

( * ) Notice: Subject to any disclaimer, the term of this patent is extended or adjusted under 35 U.S.C. 154(b) by 588 days.

(21) Appl. No.: 12/310,929

(22) PCT Filed: Sep. 13, 2007

(86) PCT No.: PCT/EP2007/059653
§ 371 (c)(1),
(2), (4) Date: Aug. 5, 2009

(87) PCT Pub. No.: WO2008/031869
PCT Pub. Date: Mar. 20, 2008

(65) Prior Publication Data
US 2009/0301170 A1  Dec. 10, 2009

(30) Foreign Application Priority Data
Sep. 13, 2006  (DE) .................. 10 2006 042 952

(51) Int. Cl.
*G01N 30/24* (2006.01)
*G05D 7/00* (2006.01)
(52) U.S. Cl. ............ 137/597; 137/102; 73/23.42; 95/89
(58) Field of Classification Search .................. 137/597, 137/102; 95/89; 73/23.42
See application file for complete search history.

(56) References Cited

U.S. PATENT DOCUMENTS

| 5,652,398 | A |   | 7/1997  | Johnson |              |
|-----------|---|---|---------|---------|--------------|
| 5,952,556 | A | * | 9/1999  | Shoji   | ........ 73/23.42 |
| 6,952,946 | B2| * | 10/2005 | Mueller | ........ 73/23.4  |
| 7,779,670 | B2| * | 8/2010  | Wang    | ........ 73/23.42 |
| 2004/0238040 | A1 | * | 12/2004 | Furukawa | ...... 137/487.5 |

FOREIGN PATENT DOCUMENTS

| EP | 0 003 617 A1 | 8/1979 |
| EP | 0 386 033 B1 | 9/1990 |
| FR | 2 664 385 A1 | 1/1992 |
| WO | WO 00/17634 A2 | 3/2000 |

OTHER PUBLICATIONS

Siemens Prozess-Gas-Cromatograph MocroSAM (Translation).*
Siemens, "Prozess-Gas-Chromatograph MicroSAM", Gerätehandbuch C79000-G5300-0560-4.1, [Online], Aug. 7, 2006, Internet: URL:http://cache.automation.siemens.com> (retrieved on Jan. 9, 2007), pp. 1-55.

* cited by examiner

*Primary Examiner* — Craig Schneider
*Assistant Examiner* — Atif Chaudry

(57) ABSTRACT

An arrangement for metering a gaseous sample in a carrier gas stream has a sample gas path and a carrier gas path, both paths being connected to a carrier gas source. By introducing different pressures into the sample gas path and the carrier gas path, a metered amount is extracted from a sample slug and diverted into the carrier gas stream via a connection gas path through the carrier gas path. The sample gas path has two flow resistances in front of and behind a branch point of a connection gas path. One resistance lies between the carrier gas source and a metering unit and a gas volume of the sample gas path between the branch point of the connection gas path and the other flow resistance is dimensioned such that the sample slug only reaches the second resistance after extraction and diversion of the metered amount.

7 Claims, 1 Drawing Sheet

ARRANGEMENT FOR METERING A GASEOUS SAMPLE IN A CARRIER GAS STREAM

CROSS REFERENCE TO RELATED APPLICATIONS

This application is the US National Stage of International Application No. PCT/EP2007/059653 filed Sep. 13, 2007 and claims the benefit thereof. The International Application claims the benefits of German patent application No. 10 2006 042 952.4 DE filed Sep. 13, 2006, both of the applications are incorporated by reference herein in their entirety.

FIELD OF INVENTION

The invention relates to an arrangement for metering a gaseous sample in a carrier gas stream.

BACKGROUND OF INVENTION

An arrangement of this type is known from EP 0 386 033 B1 or the technical manual SIEMENS: "Prozess-Gas-Chromatograph MicroSAM", [Process Gas Chromatograph MicroSAM] Edition 4.01 C79000-G5300-C560-4.1, pages 30, 31, 40 and 41, on the internet: http://cache.automation.siemens.com/dnl/jQxMTYyMwAA__17969517HB/MicroSAM% 2DManual D V41.pdf (Sep. 07, 2006).

In gas chromatography, the performance of the analysis of gas samples largely depends on the sample being introduced into the chromatographic separator (separating columns or separating column circuits). Small metered amounts in the form of short and as sharply restricted "slugs" of sample gas as possible are conveyed in the carrier gas path, which conveys the sample slug to the separator and herethrough.

To this end, the afore-cited known arrangements have a sample gas path and a carrier gas path, which are both connected to a carrier gas source with constant pressure. A controllable metering device is arranged between the carrier gas source and the sample gas path, said metering device consisting of valves and a metering loop and being used for feeding a wide, unsharp sample gas slug into the carrier gas stream through the sample gas path. A device for introducing different pressures into the sample gas path and the carrier gas path allows a small metered amount to be extracted from the sample slug in the sample gas path by way of a connection gas path between both gas paths and to be conveyed into the carrier gas stream through the carrier gas path. From there, the now short and sharply restricted sample slug reaches the separator.

The introduction of the different pressures in the sample gas path and the carrier gas path is effected for instance by means of a switchable valve in the carrier gas path between the carrier gas source and the branch of the connection gas path, with a first adjustable flow resistance being arranged in the sample gas path upstream of the branch of the connection gas path and a second flow resistance being arranged therebehind. The flow resistances are used to determine the pressure conditions in each of the two positions of the valve and thus to prevent sample gas from leaving the sample path in the carrier gas path unintentionally for instance.

SUMMARY OF INVENTION

An object of the invention is to further increase the metering accuracy.

In accordance with the invention, the object is achieved by the arrangement specified in the claim. Accordingly, provision is made for the first flow resistance to lie between the carrier gas source and the metering device and for the gas volume of the sample gas path between the branch of the connection gas path and the second flow resistance to be dimensioned in such a way that the sample slug only reaches the second flow resistance after the extraction and diversion of the metered amount.

The invention relates to the knowledge that the carrier gas and the gaseous sample have different viscosities and the viscosity of the sample is also dependent on the composition thereof so that different flow speeds result in the flow resistances depending on the viscosity of the flowing gas. The inventive arrangement now ensures that during the metering process, in other words during the extraction and diversion of the desired metered amount from the wide sample slug, no sample gas flows through one of the flow resistances, so that the flow speed and thus the metered sample amount is independent of the viscosity of the sample.

BRIEF DESCRIPTION OF THE DRAWINGS

To further explain the invention, reference is made below to the Figures of the drawing, which show an exemplary embodiment of the arrangement according to the invention in four different operating phases.

DETAILED DESCRIPTION OF INVENTION

Figure 1:
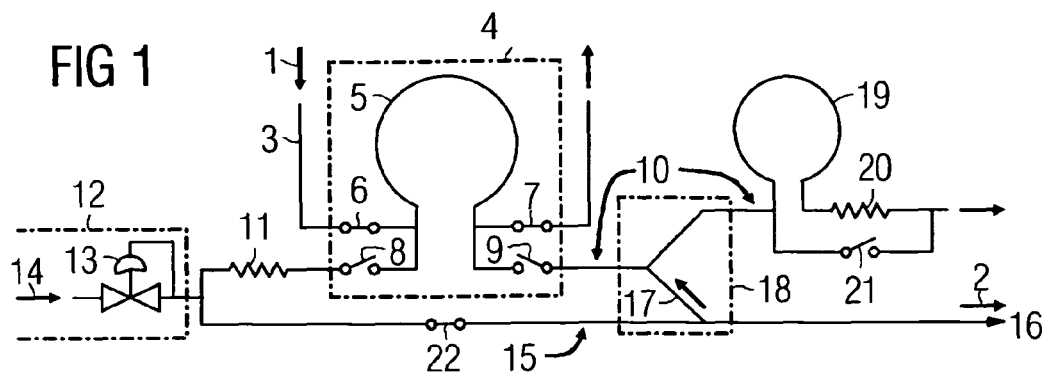

FIGS. 1 to 4 show by way of example an arrangement for metering a sample (mixture of substances) 1 in a carrier gas stream 2 for a subsequent gas chromatographic analysis. To this end, the sample 1 is taken from a technical process for instance and is prepared, e.g. evaporated before it enters a bypass 3 with a metering device 4 located therein. The metering device 4 consists of a metering loop 5, which can be connected in the bypass 3 by way of controllable valves 6, 7. Further controllable valves 8, 9 allow the metering loops 5 to switch in a sample gas path 10, which is connected to a carrier gas source 12 by way of a first flow resistance 11. The carrier gas source 12 contains a pressure controller 13, which keeps the pressure of the carrier gas 14 constant. A carrier gas path 15 is also connected to the carrier gas source 12, said carrier gas path 15 leading to a gas chromatographic separator 16 (not shown in further detail here), in which the mixture of substances of the sample 1 is separated and then detected. The sample gas path 10 is connected to the carrier gas path 15 behind the metering device 4 by way of a connection gas path 17. The flow divider 18 thus formed can be embodied in a known manner (EP 0 386 033 B1 or WO 00/17634, FIG. 2). During the course of the sample gas path 10, a gas volume 19 of a predetermined size and then a second flow resistance 20 are arranged respectively behind the branch of the connection gas path 17 before the gases are evacuated from the sample gas path 10. The gas volume 19 and the second flow resistance 20 can be short-circuited by way of a further controllable valve 21. An additional controllable valve 22 is finally arranged between the carrier gas source 12 and the branch of the connection gas path 17 during the course of the carrier gas path 15. The valves 6 to 9, 21, 22 can be embodied in a different fashion e.g. as microvalves, the valves 6 to 9, in particular also as rotary valves (WO 00/17634, FIG. 2).

FIG. 1 shows the inventive arrangement in a first operating phase, in which the valves 6, 7, 22 shown in simplified form as switches are opened (i.e. switches closed) and the valves 8, 9, 21 are closed (i.e. switches open). In this operating phase, the metering loop 5 is filled with the sample 1, while the carrier gas 15 flows into the separator 16 by way of the carrier gas path 14. A small part of the carrier gas 14 enters the sample gas path 10 by way of the connection gas path 17, and is emptied there by way of the gas volume 19 and the second flow resistance 20. The gas flow in the connection gas path 17 prevents gas from entering the carrier gas path 15 and the separator 16 from the sample gas path 10.

Figure 2:
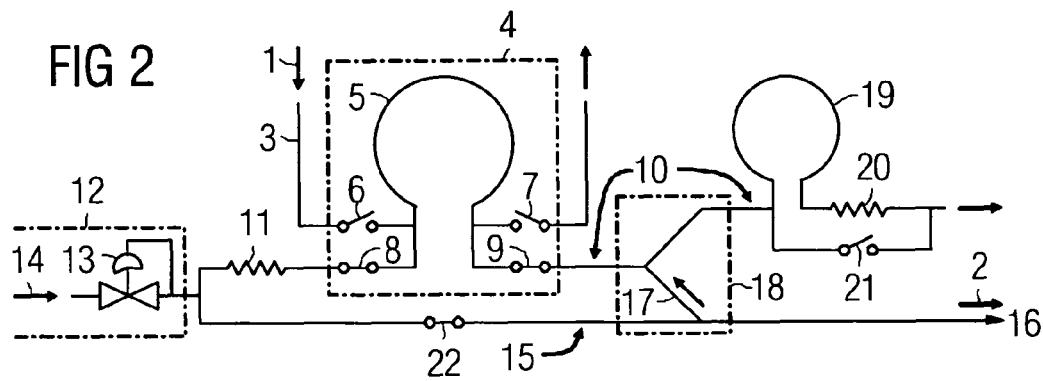

In the operating phase shown in FIG. 2, the valves 8, 9, 22 are opened (i.e. switches closed) and the valves 6, 7, 21 are closed (i.e. switches open). In this way the sample amount contained in the metering loop 5 is routed through the sample gas path 10 by means of the carrier gas 14 as a wide sample gas slug. Similarly in the operating phase shown in FIG. 1, the gas flow in the connection gas path 17 prevents gas from entering the carrier gas path 15 and the separator 16 from the sample gas path 10.

Figure 3:
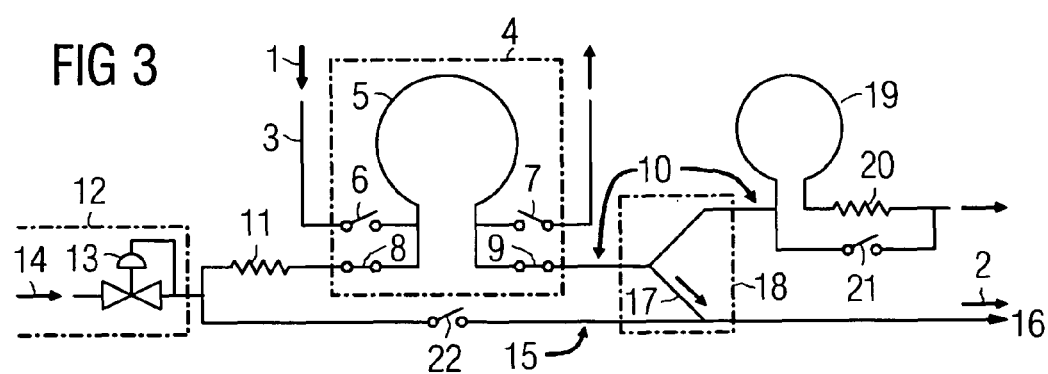

If the sample gas slug enters the region of the branch of the connection gas path 17, the valve 22 is closed for a brief predetermined period of time, as shown in FIG. 3, (i.e. switches open) so that the pressure conditions in the sample gas path 10 and the carrier gas path 15 change and the gas flow in the connection gas path 17 reverses. As a result, a small metered amount is extracted from the wide sample slug in the sample gas path 10 and is guided into the carrier gas stream through the carrier gas path 15 to the separator 16 as a sharply restricted short sample slug.

As a result of the first flow resistance 11 lying between the carrier gas source 12 and the metering device 4, and the gas volume 19 of the sample gas path 10 between the branch of the connection gas path 17 and the second flow resistance 20 being dimensioned such that the wide sample slug only reaches the second flow resistance 20 after extraction and diversion of the metered amount, it is ensured that during the metering process, in other words during the extraction and diversion of the desired metered amount from the wide sample slug, no sample gas flows through one of the flow resistances 11, 20, so that the flow speed and thus the metered sample amount is independent of the viscosity of the sample 1.

Figure 4:
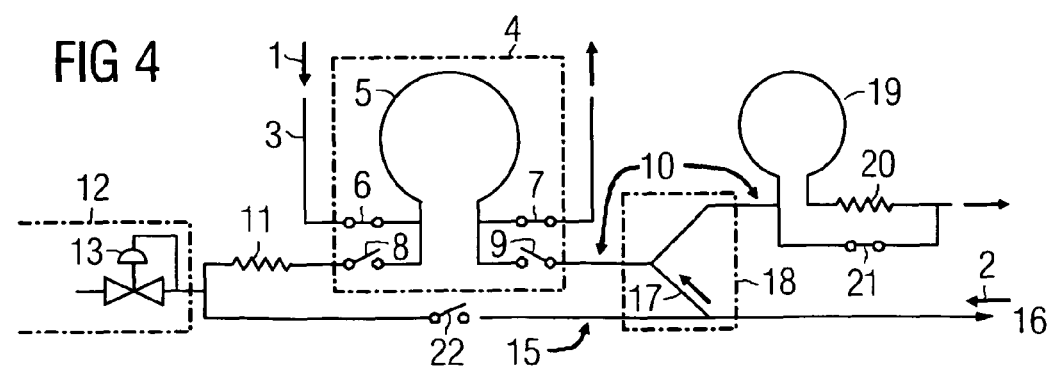

In the operating phase shown in FIG. 4, the valves 6, 7, 21 are opened (i.e. switches closed) and the valves 8, 9, 22 are closed (switches open). In this operating state, the separator 16 is backflushed via the connection gas path 17 and the outlet of the sample gas path 10.

The invention claimed is:

1. An arrangement for metering a gaseous sample in a carrier gas stream comprising:
   a sample gas path;
   a carrier gas path;
   a carrier gas source of constant pressure, the sample gas path and the carrier gas path both being connected to the carrier gas source;
   a controllable metering device arranged between the carrier gas source and the sample gas path for feeding a sample gas slug into a carrier gas stream through the sample gas path;
   a connection gas path between the sample gas path and the carrier gas path;
   a device for introducing different pressures in the sample gas path and the carrier gas path for extracting and diverting a metered amount from the sample gas slug by way of the connection gas path into the carrier gas stream through the carrier gas path;
   a first flow resistance in the sample gas path between the carrier gas source and the metering device so that no portion of the sample gas slug flows through the first flow resistance;
   a second flow resistance in the sample gas path downstream of the branch of the connection gas path;
   wherein a gas volume of the sample gas path between the branch of the connection gas path and the second flow resistance is dimensioned such that no portion of the sample gas slug flows through the second flow resistances when the metered amount is extracted and diverted from the sample gas slug.

2. An arrangement for metering a gaseous sample in a carrier gas stream comprising:
   a carrier gas source of constant pressure, a sample gas path and a carrier gas path each connected to the carrier gas source;
   a controllable metering device comprising a metering loop arranged between the carrier gas source and the sample gas path for feeding a sample gas slug into the sample gas path by filling the metering loop with the sample gas slug, and passing a carrier gas through the metering loop;
   a first flow resistance in the sample gas path between the carrier gas source and the metering device so that no portion of the sample gas slug flows through the first flow resistance;
   a connection gas path between the sample gas path and the carrier gas path downstream of the metering device;
   a controllable valve in the carrier gas path, wherein when the controllable valve is closed, a metered amount of the sample gas slug is extracted and diverted from the sample gas path to the carrier gas path via the connection gas path;
   a gas volume of the sample gas path downstream of the connection gas path; and
   a second flow resistance in the sample gas path downstream of the gas volume of the sample gas path;
   wherein the gas volume is dimensioned such that no portion of the sample gas slug flows through the second flow resistances when the metered amount of the sample gas slug is being extracted and diverted.

3. The arrangement of claim 2, wherein only a carrier gas passes through the first flow resistance.

4. The arrangement of claim 2, wherein when the controllable valve is opened, a portion of the carrier gas flows from the carrier gas path to the sample gas path via the connection gas path.

5. The arrangement of claim 2, wherein the controllable metering device comprises a series of valves which are opened and closed to provide a flow of sample gas and carrier gas through the metering loop to the sample gas path.

6. The arrangement of claim 2, wherein the sample gas slug only reaches the second flow resistance after the metered amount has been extracted and diverted.

7. An arrangement for metering a gaseous sample in a carrier gas stream comprising:
   a carrier gas source;
   a carrier gas path comprising a carrier gas path valve disposed between the carrier gas source and a gas chromatographic separator;
   a sample gas path connected to the carrier gas path upstream of the carrier gas path valve and comprising in flow direction order a first flow resistance, a metering device, a gas volume, and a second flow resistance;
   a connection gas path connected between the sample gas path and the carrier gas path, connecting to the sample gas path between the metering device and the gas volume, and connecting to the carrier gas path between the carrier gas path valve and the gas chromatographic separator, a sample gas path valve disposed in the sample gas path between the first flow resistance and the connection gas path;

a means for introducing a wide sample gas slug into the metering device;

wherein, when the sample gas path valve is opened and the carrier gas path valve is opened, the wide sample gas slug begins to move through the sample gas path toward the second flow resistance; and when the carrier gas path valve is then closed, a sharply restricted short sample slug portion of the wide sample gas slug is caused to flow through the connection gas path into the carrier gas path toward the gas chromatographic separator without any of the wide sample gas slug flowing through either the first or second flow resistances.

* * * * *